US008322342B2

(12) United States Patent
Soto et al.

(10) Patent No.: US 8,322,342 B2
(45) Date of Patent: Dec. 4, 2012

(54) OPERATIVE ARM SUPPORT

(75) Inventors: Orlando Soto, Acton, MA (US); Dustin T. Libby, North Andover, MA (US); Thomas K. Skripps, Acton, MA (US)

(73) Assignee: Allen Medical Systems, Inc., Batesville, IN (US)

(*) Notice: Subject to any disclaimer, the term of this patent is extended or adjusted under 35 U.S.C. 154(b) by 393 days.

(21) Appl. No.: 12/508,389

(22) Filed: Jul. 23, 2009

(65) Prior Publication Data

US 2010/0018537 A1 Jan. 28, 2010

Related U.S. Application Data

(60) Provisional application No. 61/083,609, filed on Jul. 25, 2008.

(51) Int. Cl.
*A61G 15/00* (2006.01)
*A47C 17/86* (2006.01)
*A61F 13/00* (2006.01)

(52) U.S. Cl. ................................ 128/845; 5/646; 602/62

(58) Field of Classification Search .................. 128/845, 128/869, 870, 875, 878, 879, 881; 5/623, 5/624, 648, 651, 658, 646, 647; 602/36, 602/62, 63

See application file for complete search history.

(56) References Cited

U.S. PATENT DOCUMENTS

| | | | |
|---|---|---|---|
| 3,046,072 | A | 7/1962 | Douglass, Jr. et al. |
| 4,431,329 | A | 2/1984 | Baitelle |
| 4,464,780 | A | 8/1984 | Ruiz |
| 4,579,324 | A | 4/1986 | McConnell |
| 4,702,465 | A | 10/1987 | McConnell |
| 4,772,002 | A | 9/1988 | McConnell et al. |
| 4,807,618 | A | 2/1989 | Auchinleck et al. |
| 4,807,864 | A | 2/1989 | Young |
| 4,809,687 | A | 3/1989 | Allen |
| 4,858,903 | A | 8/1989 | Tari et al. |
| 4,863,133 | A | 9/1989 | Bonnell |
| 4,909,264 | A | 3/1990 | Wadsworth, III et al. |
| 4,940,218 | A | 7/1990 | Akcelrod |

(Continued)

FOREIGN PATENT DOCUMENTS

WO WO 8910103 A1 11/1989

OTHER PUBLICATIONS

Partial Search Report for EP 09 25 1868 dated Aug. 4, 2010, (3 pages).

*Primary Examiner* — Patricia Bianco
*Assistant Examiner* — Ophelia Hawthorne
(74) *Attorney, Agent, or Firm* — Barnes & Thornburg, LLP

(57) ABSTRACT

A limb positioner includes a multi-axis positioner, a lock supporting the multi-axis positioner, and a limb support. The multi-axis positioner includes a variable resistance locking mechanism adjustable to vary the resistance of each axis to movement, the multi-axis positioner including a first pivot pivotable about a first axis. The limb support is supported by the multi-axis positioner and includes a frame configured to support a limb such that a joint of the limb is indexed to the first pivot for movement of the limb about the joint. The limb support includes disposable dressing positioned on the first and second extensions, the disposable dressing including a plurality of flexible restraints for securing the limb of a patient to the limb support.

19 Claims, 11 Drawing Sheets

U.S. PATENT DOCUMENTS

| | | | |
|---|---|---|---|
| 4,941,464 | A | 7/1990 | Scott |
| 4,958,816 | A | 9/1990 | Chaney et al. |
| 4,961,610 | A | 10/1990 | Reeder et al. |
| 4,966,167 | A | 10/1990 | Jacbos et al. |
| 4,971,037 | A | 11/1990 | Pelta |
| 5,003,967 | A * | 4/1991 | McConnell ..................... 602/21 |
| 5,012,539 | A | 5/1991 | Grigg |
| 5,027,799 | A * | 7/1991 | Laico et al. ..................... 602/20 |
| 5,042,508 | A | 8/1991 | Richard |
| 5,074,291 | A | 12/1991 | Carter |
| 5,104,103 | A | 4/1992 | Auchinleck et al. |
| 5,135,210 | A | 8/1992 | Michelson |
| 5,140,998 | A | 8/1992 | Vickers |
| 5,156,168 | A | 10/1992 | Canterna |
| 5,191,903 | A | 3/1993 | Donohue |
| 5,291,903 | A | 3/1994 | Reeves |
| 5,318,509 | A | 6/1994 | Agbodoe |
| 5,372,145 | A | 12/1994 | Berger |
| 5,467,782 | A | 11/1995 | Wiseman |
| 5,509,160 | A | 4/1996 | Schubert |
| 5,547,463 | A | 8/1996 | Hinchliffe et al. |
| 5,549,121 | A | 8/1996 | Vinci |
| 5,560,577 | A | 10/1996 | Keselman |
| 5,560,728 | A | 10/1996 | McFadden |
| 5,566,681 | A | 10/1996 | Manwaring et al. |
| 5,582,379 | A | 12/1996 | Keselman et al. |
| 5,645,079 | A | 7/1997 | Zahiri et al. |
| 5,658,315 | A | 8/1997 | Lamb et al. |
| 5,718,671 | A | 2/1998 | Bzoch |
| 5,730,152 | A | 3/1998 | Esser |
| 5,735,806 | A | 4/1998 | Leibovic |
| 5,738,675 | A | 4/1998 | Botimer |
| 5,742,962 | A | 4/1998 | Yoshino et al. |
| 5,742,963 | A | 4/1998 | Trevino et al. |
| 5,775,334 | A | 7/1998 | Lamb et al. |
| 5,813,977 | A | 9/1998 | Hinchliffe et al. |
| 5,839,136 | A | 11/1998 | Vance et al. |
| 5,864,902 | A | 2/1999 | Rogers |
| 5,881,730 | A | 3/1999 | Burger |
| 5,888,190 | A | 3/1999 | Meyer et al. |
| 5,899,425 | A | 5/1999 | Corey, Jr. et al. |
| 5,918,330 | A | 7/1999 | Navarro et al. |
| 5,957,135 | A | 9/1999 | Molina |
| 5,961,085 | A | 10/1999 | Navarro et al. |
| 5,961,512 | A | 10/1999 | Purnell |
| 5,997,494 | A | 12/1999 | Watkins et al. |
| 6,000,402 | A | 12/1999 | Able |
| 6,003,175 | A | 12/1999 | Couch |
| 6,042,604 | A | 3/2000 | Gennetti |
| 6,055,987 | A | 5/2000 | Griesbach et al. |
| 6,083,182 | A | 7/2000 | Fries |
| 6,154,902 | A | 12/2000 | Russillio et al. |
| 6,438,777 | B1 | 8/2002 | Bender |
| 6,467,487 | B1 | 10/2002 | Rios |
| 6,488,621 | B1 | 12/2002 | Rullo et al. |
| 6,502,261 | B1 | 1/2003 | Harwood |
| 6,533,744 | B1 | 3/2003 | Stanish et al. |
| 6,553,995 | B1 | 4/2003 | Cole et al. |
| 6,568,010 | B1 | 5/2003 | Ames |
| 6,575,653 | B1 | 6/2003 | Krauter |
| 6,616,604 | B1 | 9/2003 | Bass et al. |
| 6,629,944 | B2 * | 10/2003 | Smart ............................. 602/36 |
| 6,704,959 | B2 | 3/2004 | Schuerch |
| 6,718,581 | B2 | 4/2004 | Riach |
| 6,725,481 | B1 | 4/2004 | Marshall |
| 6,811,541 | B2 | 11/2004 | Lambert |
| 6,826,794 | B2 | 12/2004 | Mahoney et al. |
| 7,234,180 | B2 | 6/2007 | Horton et al. |
| 7,836,890 | B2 * | 11/2010 | Waterman ..................... 128/878 |
| 2001/0039680 | A1 | 11/2001 | Boucher et al. |
| 2002/0128577 | A1 | 9/2002 | Smart |

* cited by examiner

OPERATIVE ARM SUPPORT

CROSS-REFERENCE TO RELATED APPLICATIONS

This application claims the benefit of U.S. Provisional Application Ser. No. 61/083,609, filed Jul. 25, 2008, which is hereby incorporated by reference herein.

BACKGROUND

The present disclosure is related to a limb support for surgical applications. More specifically, the present disclosure is related to an operative arm support suitable for supporting an arm during surgical operations on the shoulder of an individual.

Surgical limb holders are used to support a patient's extremities to allow a surgeon to have access to surgical sites. During joint surgeries, for example, the limb is often repositioned multiple times during the surgical process to allow the surgeon varying access to the joint supporting the limb. Because the surgical process requires access to the joint from multiple directions to allow the surgeon complete access to the joint, limb must be repositioned to change the angle from which the surgeon approaches the joint during the surgery. During some shoulder surgeries, for example, a surgeon must have both anterior and posterior access to the shoulder joint while the arm remains supported.

A positioning device that is adjusted during surgery presents issues related to sterility during the process. In some devices, the controls for adjustment are positioned outside the sterile field and require a surgery technician to assist the surgeon in positioning. This sometimes results in time consuming repositioning or a less than optimal position. This also discourages the repositioning of the limb, thereby reducing the ability of the surgeon to have optimal access to the joint.

If the adjustment mechanism is within the sterile field, then provisions must be made for maintaining sterility during the procedure. Also, the device must be capable of being sterilized by steam or chemicals, for example.

SUMMARY OF THE INVENTION

The present application discloses one or more of the features recited in the appended claims and/or the following features which, alone or in any combination, may comprise patentable subject matter:

A limb positioner comprises a multi-axis positioner, a lock supporting the multi-axis positioner, and a limb support. The multi-axis positioner includes a variable resistance locking mechanism adjustable to vary the resistance of each axis to movement, the multi-axis positioner including a first pivot pivotable about a first axis. The lock is movable between a first position wherein the multi-axis positioner is movable relative to the lock and a second position wherein the multi-axis positioner is fixed relative to the lock. The limb support is supported by the multi-axis positioner and includes a frame configured to support a limb such that a joint of the limb is indexed to the first pivot for movement of the limb about the joint.

In some embodiments the variable resistance locking mechanism is adjustable to a position wherein movement about each axis of the multi-axis positioner is resisted at a rate that prevents a limb supported on the limb positioner from movement under the weight of the limb while permitting a user to adjust the position of the limb by applying sufficient manual force to overcome the resistance. The locking mechanism may also be adjusted to lock the limb positioner such that the limb positioner is not manually adjustable.

In some embodiments the multi-axis positioner comprises first and second spherical joints, first and second arms coupled to each of the respective first and second spherical joints, and a hub interposed between the first and second arms, the first arm pivotable relative to the second arm. The multi-axis positioner may include a handle positioned on the hub and actuable by user, the handle operable to vary the resistance to movement of the first and second spherical joints and the hub.

In some embodiments pivoting of the limb support about the first axis of the first pivot permits an extremity of the limb to move about the joint without causing movement of an axis of the joint. In some embodiments, the limb supported is an arm and the joint is an elbow and movement of the forearm about the elbow does not cause movement of the patient's upper arm connected to the elbow.

In some embodiments the limb positioner further comprises a disposable dressing secured to the limb support. The disposable dressing may include means for securing the forearm of the patient to the limb support. In some embodiments, the means for securing the forearm of the patient to the limb support includes a plurality of straps and fasteners, the straps positionable to overlie the forearm and the fasteners securing the straps to maintain the forearm positioned on the limb support.

In some embodiments the disposable dressing is secured to the limb support and includes a plurality of straps, each strap including a first fastener, each of the first fasteners engageable with a second fastener of the disposable dressing such that the straps are positioned to secure the limb of a patient to the limb support. In some embodiments, the first fastener comprises a first portion of a hook-and-loop fabric fastener and the second fastener comprises a second portion of the hook-and-loop fabric fastener.

The limb support may comprise a frame including a mount, a cross-bar, a first extension, and a second extension. The mount may have a longitudinal length defining a longitudinal axis. The cross-bar may be coupled to the mount with the cross-bar having a longitudinal length defining a longitudinal axis. The first extension may have a longitudinal length defining a longitudinal axis and may be coupled to the cross-bar at a position spaced apart from the mount. The first extension extends from the cross-bar in a cantilevered configuration such that the longitudinal axis of the first extension may be generally perpendicular to both the longitudinal axis of the cross-bar and the longitudinal axis of a the mount. The second extension may have a longitudinal length defining a longitudinal axis and may be coupled to the cross-bar at a position spaced apart from the mount and opposite the first extension. The second extension extends from the cross-bar in a cantilevered configuration such that the longitudinal axis of the second extension may be generally perpendicular to both the longitudinal axis of the cross-bar and the longitudinal axis of a the mount. The longitudinal axis of the second extension may be generally parallel to the longitudinal axis of the first extension, a space being formed between the first extension and the second extension.

In some embodiments the mount has a cavity sized to be received on a supporting structure for the mount.

The limb support may further comprise a spacer between the cross-bar and each of the first and second extensions. In some embodiments, the longitudinal axes of the first and second extensions are spaced apart from the longitudinal axis of the cross-bar such that the longitudinal axes of the first and second extensions do not intersect the longitudinal axis of the cross-bar. The limb support may be sterilizable.

In some embodiments, the disposable dressing may be positioned on the first and second extensions, the disposable dressing including a plurality of flexible restraints for securing the limb of a patient to the limb support.

In some embodiments the disposable dressing may include a flexible base having a bottom surface and a top surface, an envelope having an open end, the envelope sized to enclose the first and second extensions, a fastener securing the disposable dressing to the frame, a flap coupled to the flexible base, the flap positionable to overlie a limb supported on the flexible base, and a plurality of straps to secure the flap over the limb and secure the limb to the limb support.

In some embodiments, the straps are secured by a hook-and-loop fastener. In some embodiments, the disposable dressing comprises foam.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 2:
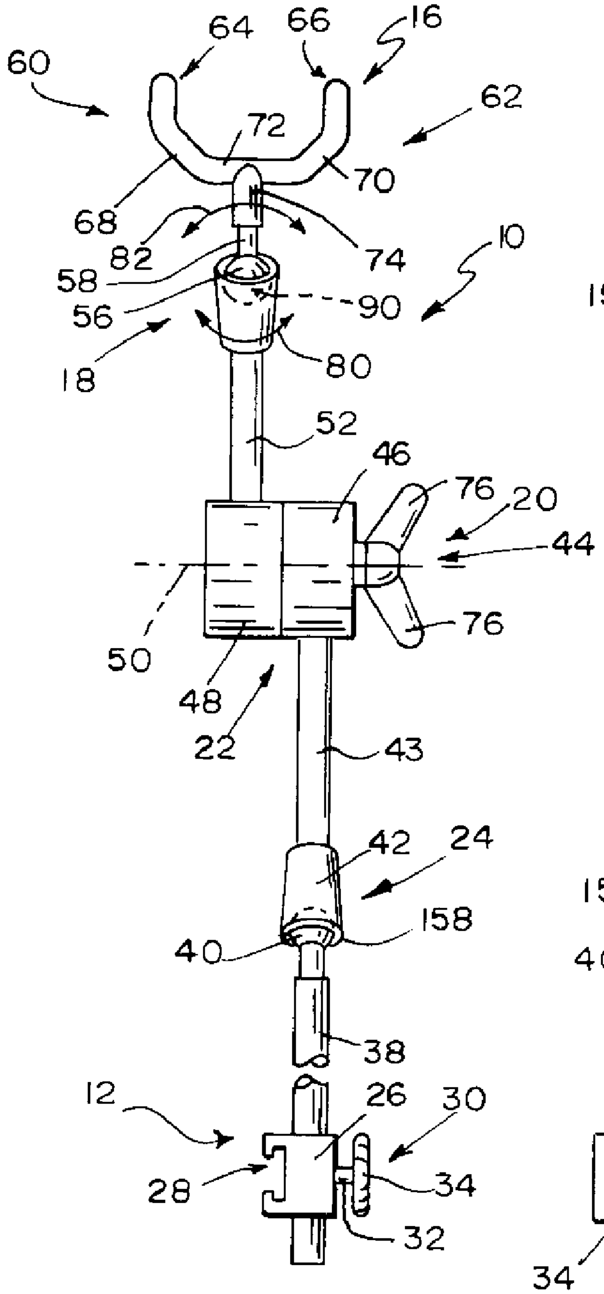
FIG. 2 is a side view of the limb positioner of FIG. 1.
Figure 1:
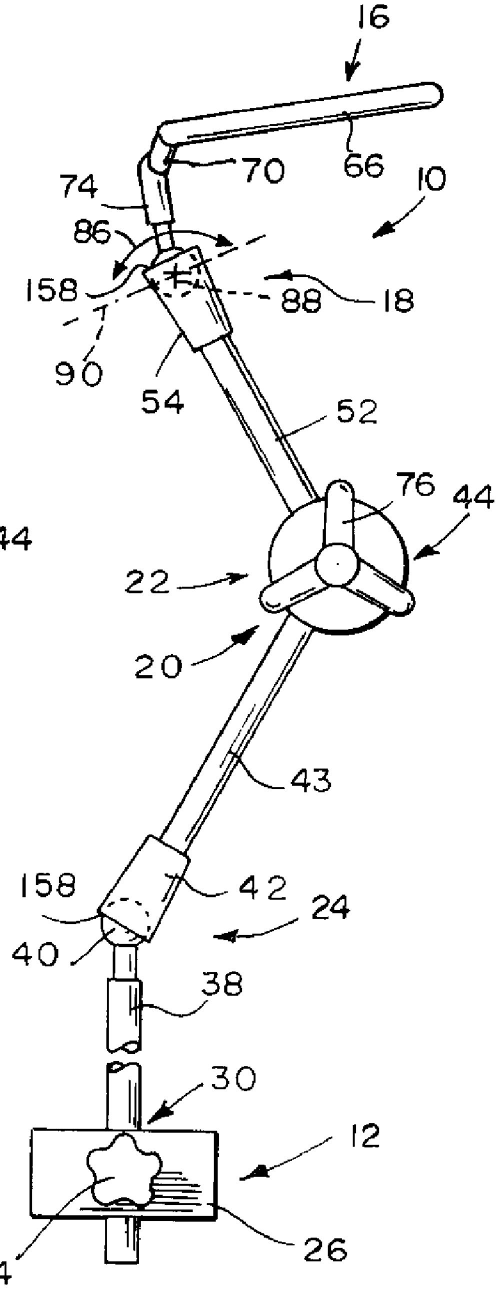
FIG. 1 is a front view of an embodiment of an limb positioner.

An embodiment of a limb positioner 10, illustratively embodied as an operative arm support is shown in FIGS. 1 and 2. A commercial embodiment of the illustrative embodiment is a part numb A-92000 positioner available from Allen Medical Systems, Acton, Mass. The limb positioner 10 includes a rail clamp 12, a multi-axis positioner 14, and a limb support 16 that is adjustable relative to the multi-axis positioner 14 through a ball joint 18. The limb positioner 10 includes a release mechanism 20 that is actuable by a user to release a plurality of joints 18, 22, and 24 to allow the limb positioner 10 to be re-positioned. When a user, such as a surgeon, for example, actuates the release mechanism 20, the user is able to reposition the limb support 16 in three-dimensional space by moving the multi-axis positioner 14 as will be discussed in further detail below. The illustrative limb positioner 10 may be used to position a limb for any of a number of procedures. The illustrative embodiment is especially effective for rotator cuff repair, SLAP lesion repair, Bankart repair, and capular release.

The rail clamp 12 has a body 26 that forms a t-slot 28. The rail clamp 12 further includes a lock 30 having a threaded axle 32 received into the body 26. The threaded axle 32 is coupled to a grip 34 movable by a user to rotate the threaded axle 32 into and out of the body 26. The rail clamp 12 is received onto a rail of a surgical table with the rail of the surgical to be engaged by the t-slot 28 of the rail clamp 12. The threaded axle 32 extends through the body 26 to engage the rail of the surgical table to lock the rail to 12 to the rail of the surgical table. The t-slot 28 is sized such that the rail clamp 12 may be connected a rail of a surgical table over a drape so that the limb positioner 10 may be completely positioned within the sterile field.

The multi-axis positioner 14 includes a support 36 having a stem 38 received into the rail clamp 12. The stem 38 is coupled to a ball 40 received in a 42 to form ball joint 24. An arm 43 is coupled to the socket 42 at one end and a hub 46 of release mechanism 20 at the opposite end. Release mechanism 20 further includes a second hub 48 pivotably coupled to hub 46 so that hub 46 and hub 48 move relative to each other with rotation about an axis 50 common to both hubs 46 and 48. Release mechanism 20 further includes a handle 44 having a plurality of grips 76 which may be gripped by a user to rotate handle 44 about axis 50.

Another arm 52 is coupled to hub 48. A socket 54 of ball joint 18 is coupled to arm 52 and receives a ball 56. A mounting stem 58 is coupled to ball 56 and extends there from to support a limb support 16 having a mount 74 received on mounting stem 58. Both ball joint 18 and ball joint 24 are configured to have multiple degrees of freedom. For example, ball joint 18 is movable as indicated by arrow 86 about an imaginary axis 88 as shown in FIG. 1. Referring now to FIG. 2, ball 56 is also rotatable about an axis 90 as indicated by arrow 82. Ball 56 is also rotatable about an axis 84 as shown in FIG. 2. The ball joint 24 operates in a manner similar to ball joint 18 having similar degrees of freedom. It should also be understood that arm 52 rotates about axis 50 such that arm 52 moves relative to arm 43 as indicated by an arrow 78 shown in FIG. 1 to change the angle between arm 52 and arm 43. The ball joints 18 and 24 are of the type that allow generally spherical movement of the stem relative to the socket.

The limb support 16 further includes a cross-bar 72 coupled to the mount 74 and two arms 60 and 62 extending away from cross-bar 72. The first arm 60 comprises a spacer 68 and an extension 64. The second arm 62 includes a spacer 70 coupled to cross-bar 72 and extending upwardly and forwardly therefrom. A second extension 66 is coupled to spacer 70 and extends there from such that extension 64 and extension 66 are generally parallel and spaced apart and provide a support structure that is cantilevered from the mount 74.

Figure 13:
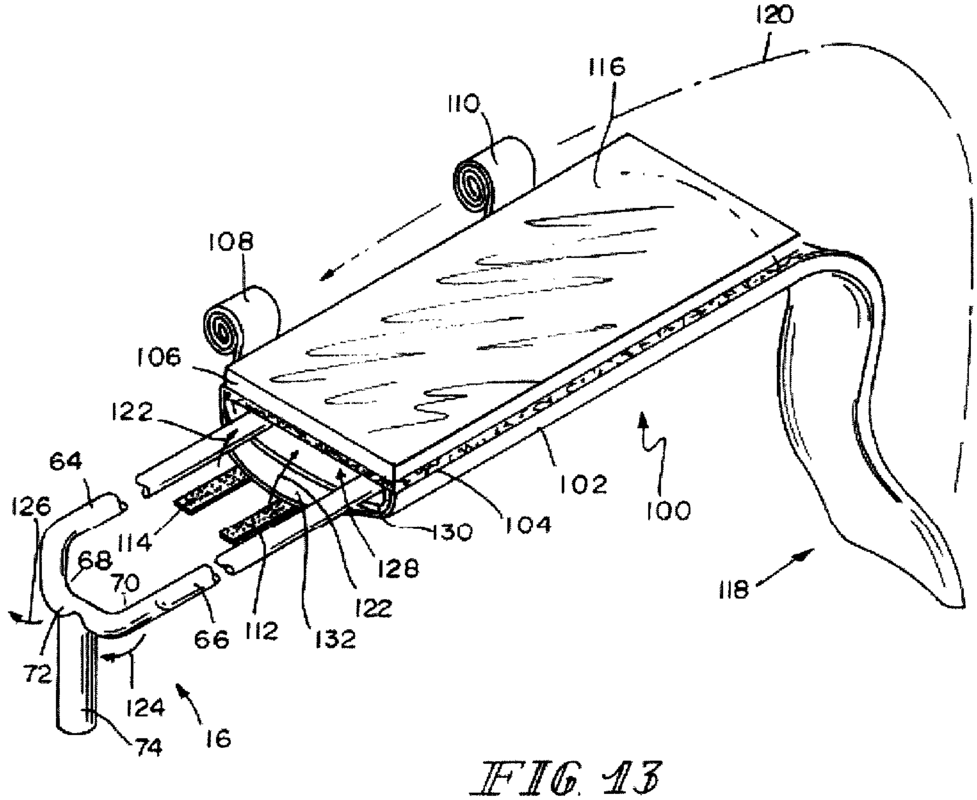
FIG. 13 is a perspective view of a limb support of the embodiment of FIG. 1, the limb support engaged with a disposable dressing.

The limb support 16 may be used with any of a number of configurations of disposable dressings for securing the limb of a patient. An embodiment of a disposable dressing 100, shown in FIG. 13, is configured for use with the limb support 16 to secure a patient's limb to the limb support 16 during surgical procedures. The disposable dressing 100 is an all fabric construction and is configured to secure a patient's limb with minimal set-up. A commercial embodiment of the disposable dressing is a part number A-92001 available from Allen Medical Systems of Acton, Mass. The disposable dressing 100 includes a layer 106 having a thickness and construction sufficient to provide a cushion between the limb of the patient and the extensions 64 and 66 of the limb support 16. The layer 106 is secured to a layer 104 which is configured to form an envelope space 128 that receives the extensions 64 and 66 to secure disposable dressing 100 from lateral movement relative to the limb support 16. Another layer 102 is secured to the layer 104 with layer 102 forming a flap 132 at the end of the disposable dressing 100 nearest the mount 74 of the limb support 16 when the disposable dressing 100 is positioned on the limb support 16. A second flap 118 extends from the end of the disposable dressing 100 opposite the mount 74.

The disposable dressing 100 also includes two fasteners 112 and 114 which are secured to the flap 132. In use, the fasteners 112 and 114 secure the disposable dressing 100 to the limb support 16 by engaging the cross-bar 72. In the illustrative embodiment, fasteners 112 and 114 comprise hook-and-loop fastener surfaces on opposite sides. When the disposable dressing 100 is engaged with the limb support 16, the fasteners 112 and 114 are wrapped about the cross-bar 72 as indicated by arrows 124 and 126 respectively. Moving the fasteners 112 and 114 in the direction of arrows 122, 122, the hooks on an upper surface of fasteners 112 and 114 are folded over to engage and upper surface 116 of layer 106 securing the disposable dressing 100 to the limb support 16.

The disposable dressing 100 further includes two straps 108 and 110 which are used to secure the limb 134 of a patient 136 (seen in FIGS. 14-16) to the disposable dressing 100 and, thereby, the limb support 16. In the illustrative embodiment shown in FIGS. 14-16, the disposable dressing 100 is used to secure the forearm 134 of the patient 136 with the hand 138 extending outwardly to allow some movement of the wrist of the patient 136. The flap 118 of disposable dressing 100 is folded over the hand 138 and forearm 134 of the patient 136 as indicated by arrow 120. The straps 108 and 110 include fasteners 140 and 142 respectively, which are illustratively embodied as hooks of a hook-and-loop fabric fastening assembly. The straps 108 and 110 are wrapped over the top of the forearm 134 of the patient 136 and fasteners 140 and 142 are secured to a lower surface 144 of the layer 102 to secure the forearm 134 to the assembly of the disposable dressing 100 and the limb support 16 as shown in FIG. 16.

Figure 14:
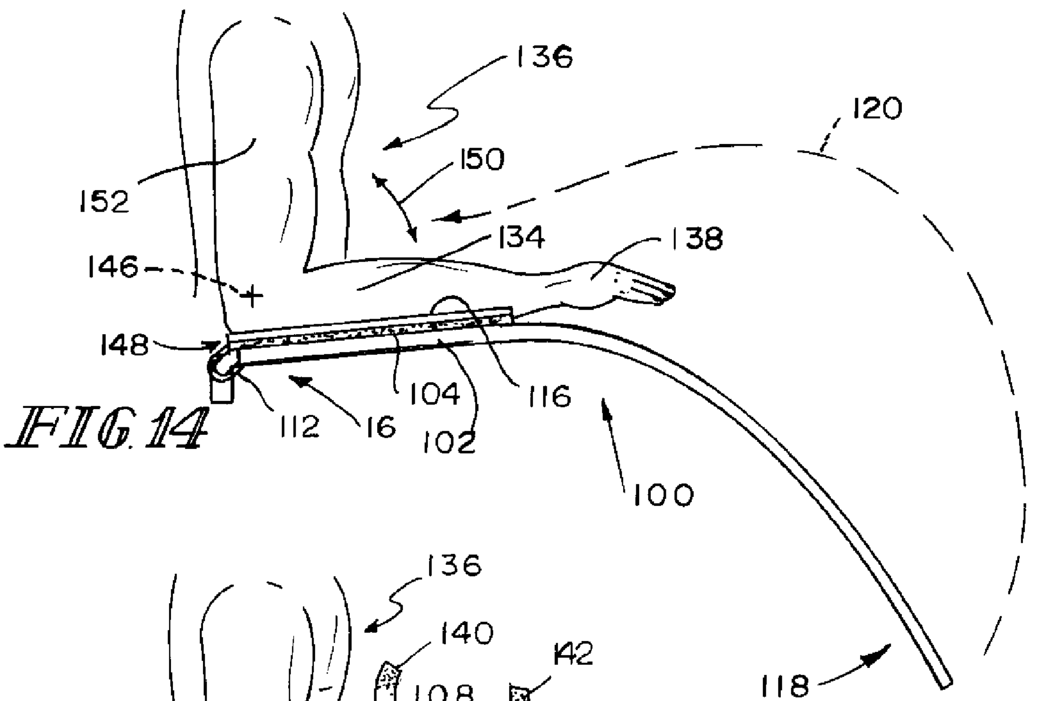
FIGS. 14-16 are side views of the limb support and dressing of FIG. 13 during various steps of engagement with the forearm of a patient, the limb support and dressing securing the forearm of the patient.
Figure 15:
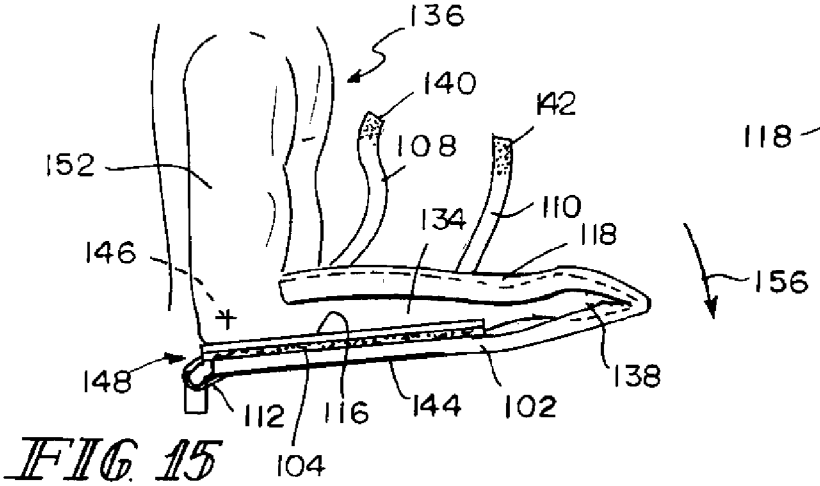
Figure 16:
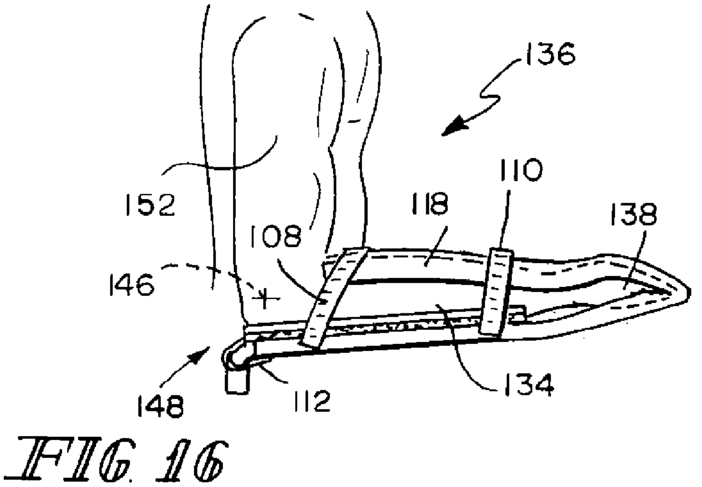

While the illustrative embodiment of FIGS. 14-16 are shown with the hand of the patient extending in a cantilevered fashion from the support of the extensions 64 and 66 of the limb support 16, it should be understood that in other embodiments, the length of the extensions 64 and 66 can be varied to support the entire limb or any portion thereof, depending on the requirements of the procedure being performed. For example, the hand 138 may be supported in some embodiments. In other embodiments, the entire arm may be supported. In addition, while the illustrative embodiment utilizes hook-and-loop fabric fasteners, in other embodiments the various portions of the disposable dressing 100 may be secured by buttons, pins, tape, or other similar fasteners. In addition, additional straps may be added to vary the location and strength of the securement of the limb 134 of the patient 136.

Referring again to FIGS. 14-16, the mount 74 is shown positioned in relation to the pivot point 146 of the elbow 148 of the patient 136 such that rotation of the mount about the center of the ball 56 (seen in FIG. 1) permits the elbow 148 to be flexed to change the angle 150 between the forearm 134 and the upper arm 152 of the patient 136. The illustrative configuration indexing movement of the limb support 16 to the elbow 148 permits a surgeon to move the patient's arm 154 through natural motion to reposition the arm 154 as necessary during surgery. For example, rotation of the patient's forearm 134 downwardly as indicated by arrow 156 in FIG. 15 results in movement of the forearm 134 relative to the pivot point 146 without causing any reaction in the upper arm 152.

Figure 10:
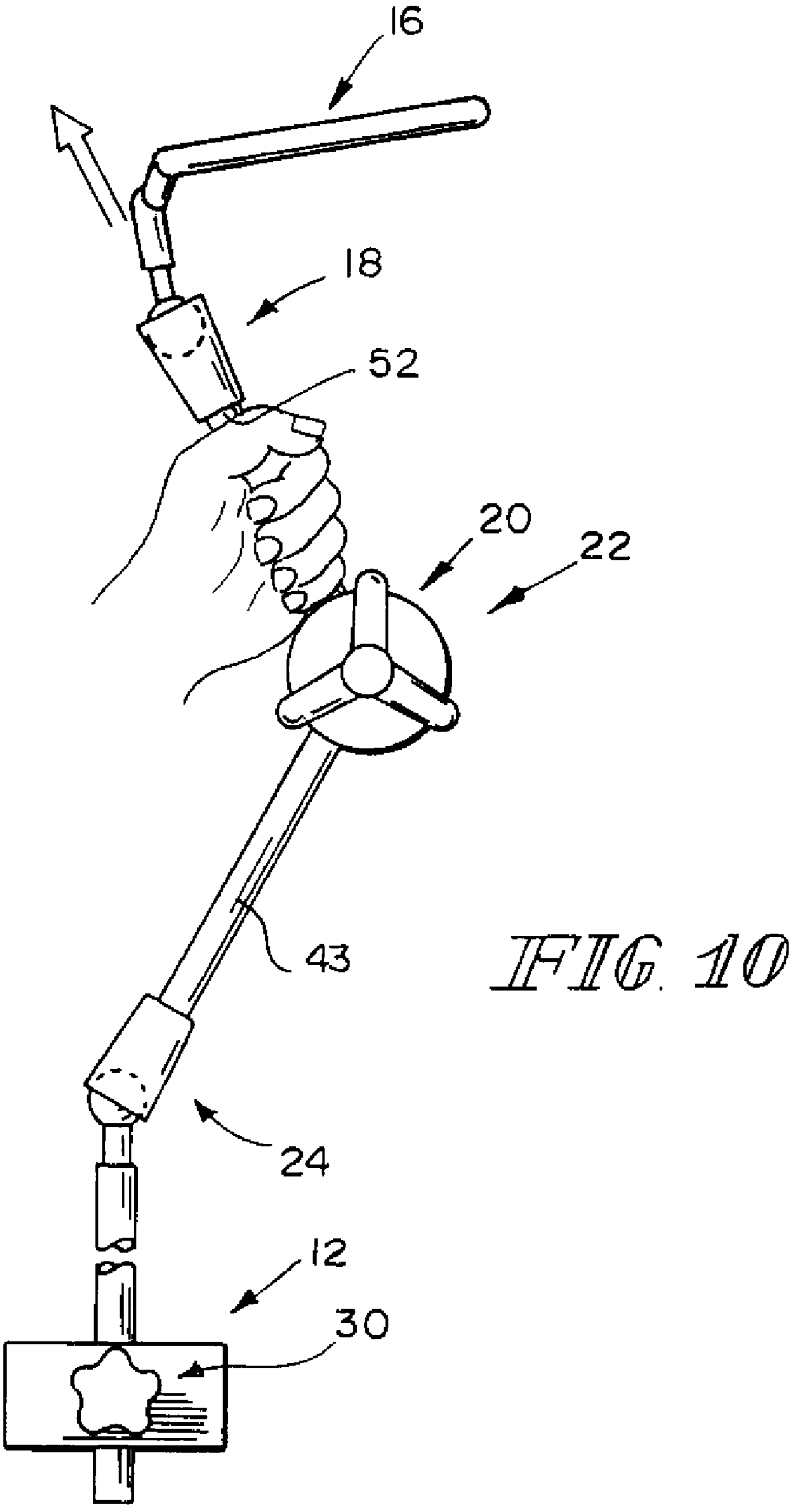
FIG. 10 is a front view of the embodiment of FIG. 1 being manually moved to adjust the position of a limb support of the limp positioner.
Figure 11:
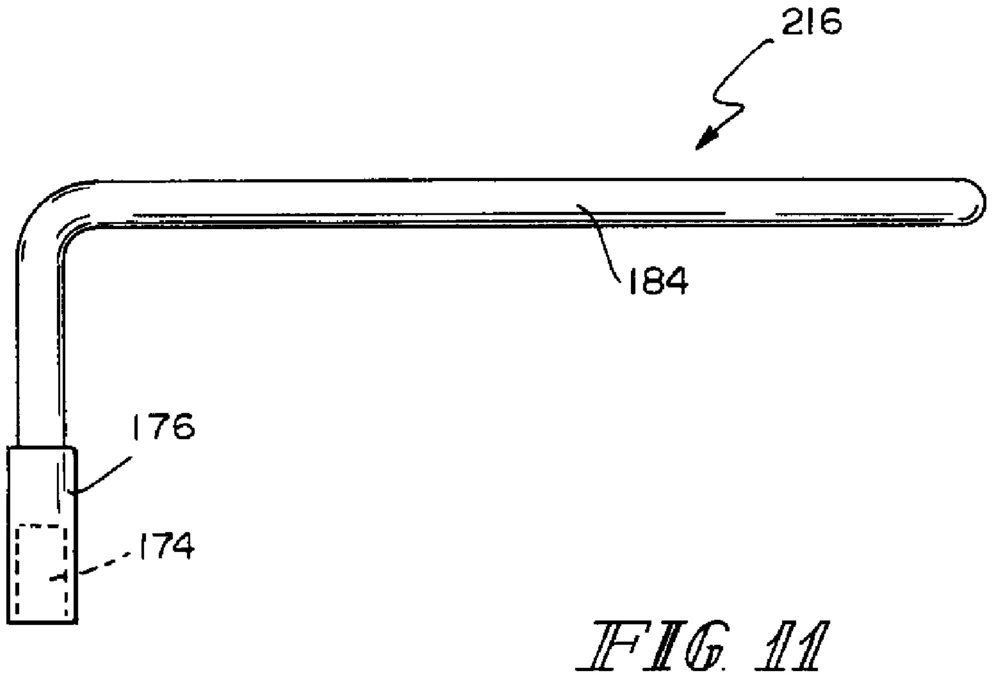
FIG. 11 is a side view of an embodiment of a limb support.
Figure 12:
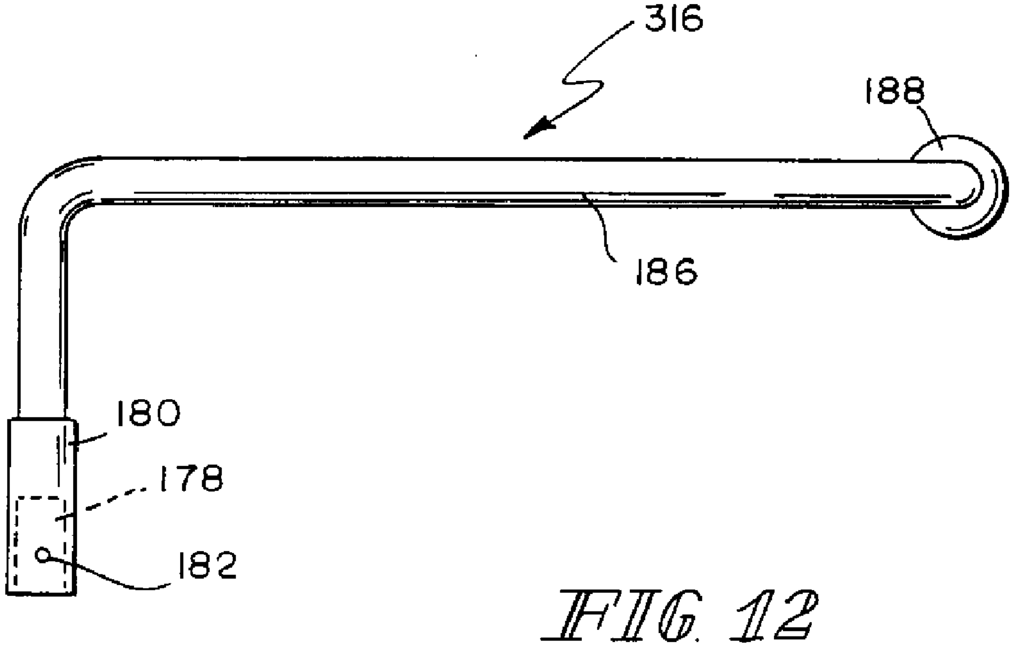
FIG. 12 is a side view of yet another embodiment of a limb support.

The release mechanism 20 of multi-axis positioner 14 acts to release all each of the joints 18, 22, and 24 to allow the multi-axis positioner 14 to be moved by hand as shown in FIG. 10. A user may release the joints 18, 22, and 24 and manually move the limb positioner 10 as necessary with the limb supported on limb support 16. The release mechanism 20 of the illustrative embodiment varies the friction in each of the joints 18, 22, and 24 so that there is sufficient resistance to movement that the limb positioner 10 will not fall under the weight of the patient's limb, but force applied by a user permits the arms 52 and 43 as well as limb support 16 to be moved to a new position. The release mechanism 20 may then be actuated by a user to secure the limb positioner 10 in the new position without risk of inadvertent movement during the remainder of the procedure. Because the entire limb positioner 10 as well as the disposable dressing 100 is sterile, a surgeon is free to re-position the limb positioner 10 during a procedure.

Figure 3:
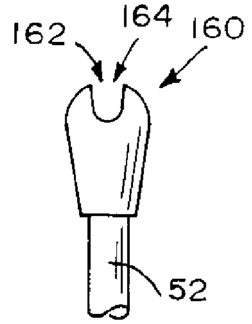
FIG. 3 is a side view of a portion of another embodiment of a limb positioner, FIG. 3 showing an alternative embodiment of a socket of a ball joint.
Figure 4:
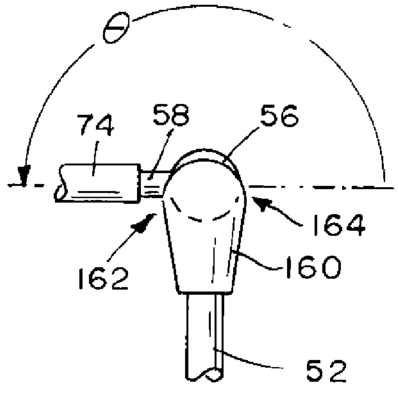
FIG. 4 is a front view of a ball joint including the socket of FIG. 3.
Figure 5:
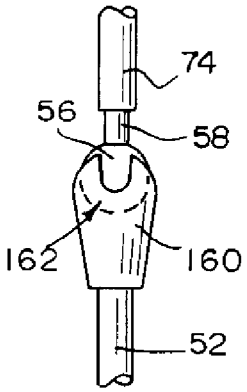
FIG. 5 is a side view of the ball joint of FIG. 4 with the ball rotated 90 degrees from the position shown in FIG. 4.

In the illustrative embodiment of FIG. 1, the socket 42 is configured with an annular upper surface 158 which provides a stop surface against which the mounting stem 58 rests. The socket 42 is similarly configured. In other embodiments, the socket 54 and the socket 42 may each be selectively omitted and replaced with another embodiment of a socket. For example, a socket 160 shown in FIGS. 3-5 is formed to include a pair of notches 162 and 164. The notches 162 and 164 are positioned in alignment to allow the stem 159 to move through an angle Θ of 180 degrees in a single plane as shown in FIG. 4. The movement of the stem 58 out of the plane is limited to an angle of less than 180 degrees because the stem 58 contacts the socket 160. When notches 162 and 164 are aligned generally perpendicular to the axis 50, the ranged of motion of the limb support 16 is limited to be maintained generally along a plane of motion coincident with the plane of motion of the axis 84 of the arm 52. The reduction in the range of movement out of this plane reduces the opportunity for misalignment of the joint supported by the limb support 16 from the joint from which it depends. For example, the movement of the elbow of a patient is maintained in general planar alignment with the shoulder of the patient during re-positioning.

Figure 6:
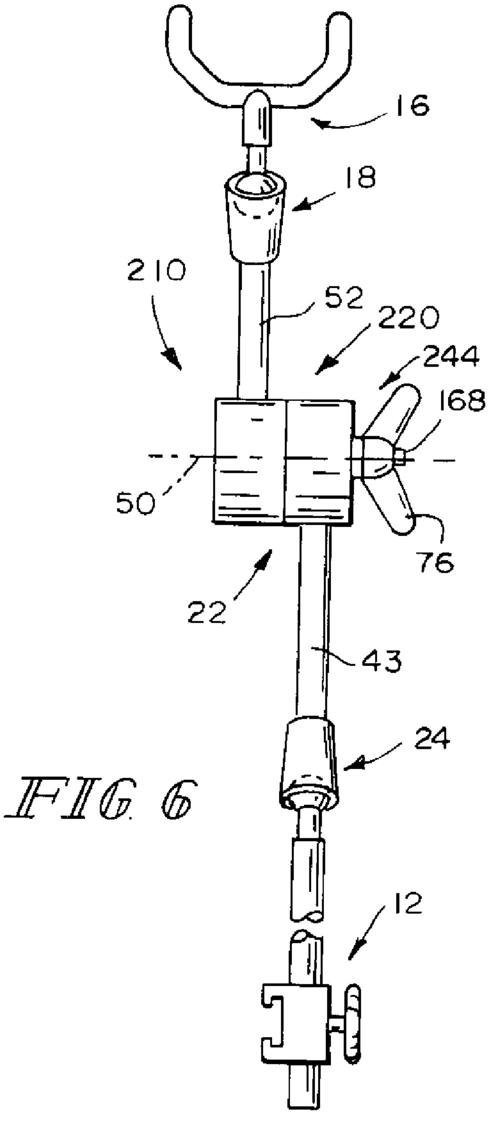
FIG. 6 is a side view of another embodiment of a limb positioner.
Figure 7:
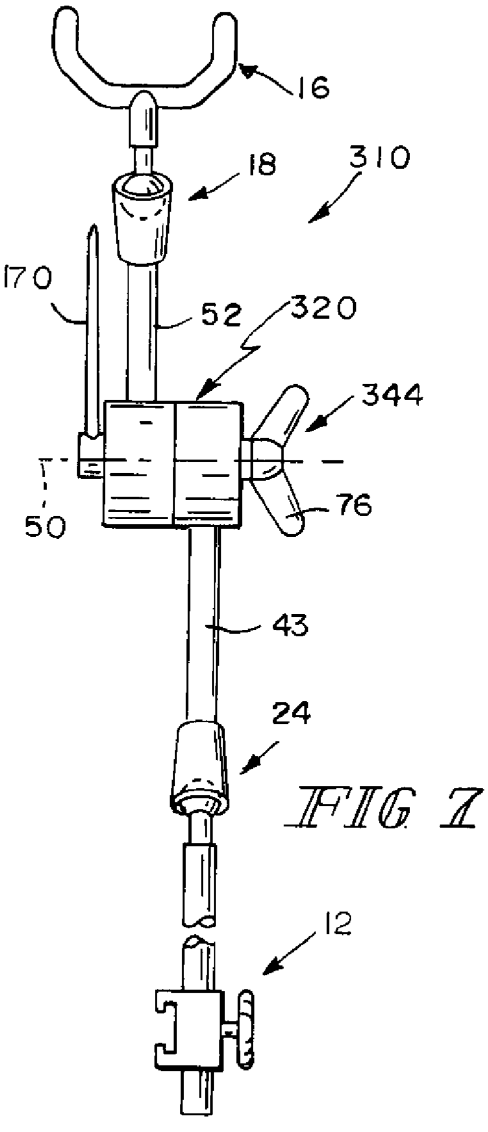
FIG. 7 is a side view of yet another embodiment of a limb positioner.
Figure 8:
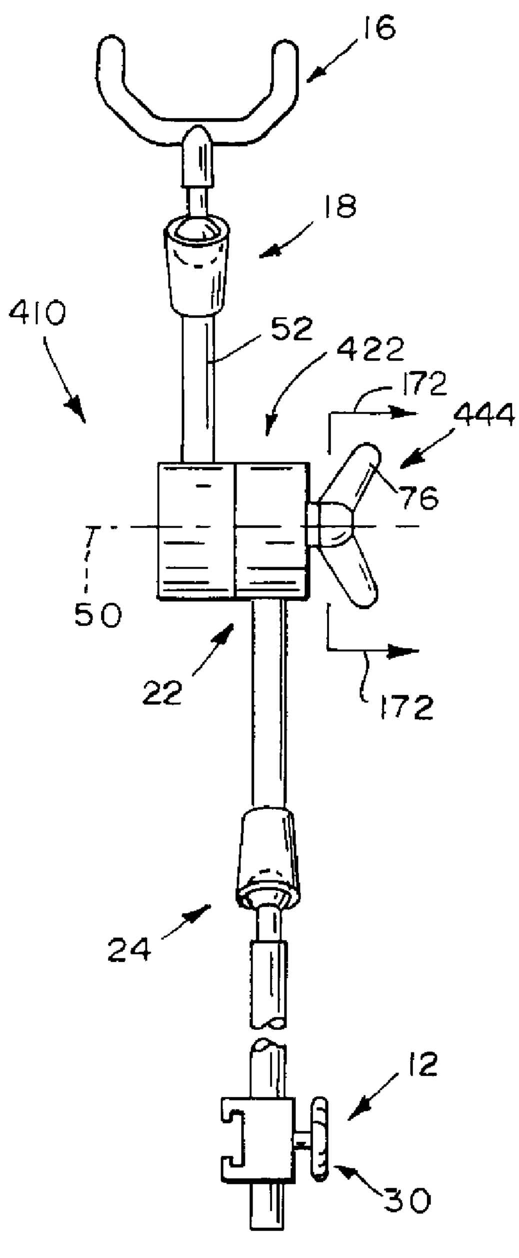
FIG. 8 is a side view of yet still another embodiment of a limb positioner.
Figure 9:
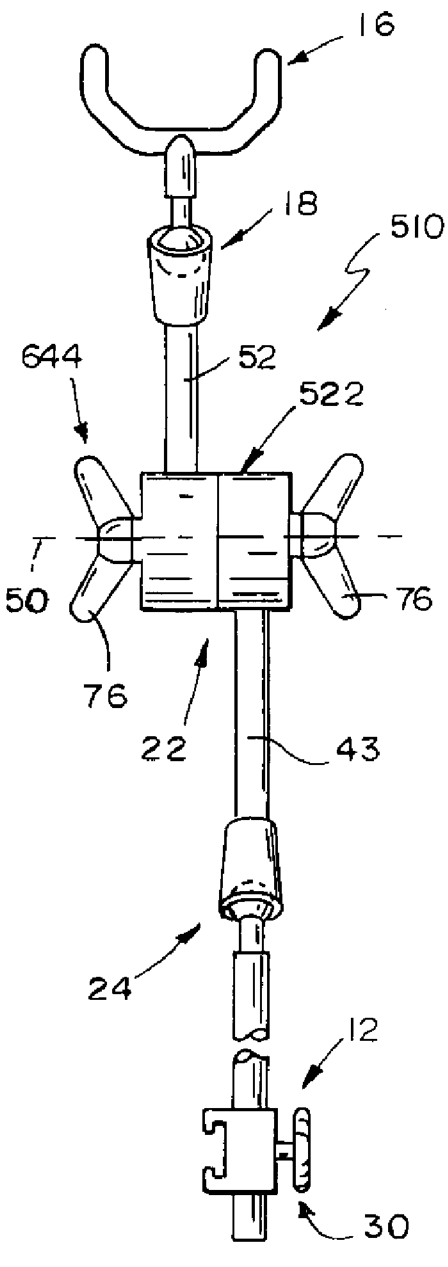
FIG. 9 is a side view of another embodiment of a limb positioner.

The release mechanism 20 of the illustrative embodiment of FIGS. 1 and 2 includes a handle 44 having grips 76. Rotation of the handle 44 about axis 50 releases and activates the release mechanism 20 with all of the joints 18, 22, and 24 being simultaneously locked and released. In another embodiment of a limb positioner 210, shown in FIG. 6, a release mechanism 244 includes a handle 244 which acts in a manner similar to handle 44 of the illustrative limb positioner 10, and further includes a quick release button 168 which may be actuated to provide complete release of the joints 18, 22 and 24 to over-ride the frictional resistance of the joints 18, 22, and 24 and permit quick re-positioning of the limb positioner 210. Releasing the quick release button 168 results in re-engagement of the frictional resistance within the joints 18, 22, and 24. Thus, if a surgeon needs to make a gross adjustment to the position of the limb supported on the limb positioner 210, the quick release button 168 is depressed while the adjustment is made and released once the new position is achieved.

In yet another embodiment, a limb positioner 310 includes a release mechanism 320 that includes a handle 344 which operates in a manner similar to the handle 44 of the limb positioner 10. The limb positioner 310 also includes a lever 170 that is actuable about axis 50 to release joints 18, 22, and 24. The lever 170 provides increased leverage for a user to lock the joints 18, 22, and 24 frictionally to prevent movement of the limb positioner 310.

In still yet another embodiment, a limb positioner 410 includes a release mechanism 422 which is actuated by a handle 444 by pulling handle 444 in the direction of arrows 172, 172.

In another embodiment, a limb positioner 510 includes a release mechanism 522 which is actuable from two sides by either a handle 544 or a handle 644 to provide access to the release mechanism 522 from multiple locations.

In another embodiment of a limb support, limb support 216 is shown to include a unitary support 184 which extends from a stem 176 and which is configured to provide universal mount for support platforms to be mounted for specific procedures. For example, a patient's limb may be strapped to the unitary support 184 and positioned relative to the mount 176 to vary the point on the limb to which the mount is indexed. The mount 176 includes a cavity 174 which is sized to receive the mounting stem 58. The cavity 174 is sized to engage the stem 58 frictionally to secure the limb support 216 relative to the stem 58.

In another embodiment, a limb support 316 includes a grip 188 mounted to a unitary support 186 with the grip 188 being positioned to allow patient to wrap their hand around the grip 188 during a procedure. Illustratively, limb support 316 includes a mount 180 having a cavity 178 similar to cavity 174 of mount 176. Mount 180 also includes a through-hole 182 through which a fastener (not shown) can be inserted to secure the mount 180 to the stem 58. For example, in some embodiments, a stem 58 may be modified such that the stem is formed to include a through-hole so that a roll pin may be inserted to secure the limb support 316 to the stem 58. The through-hole 182 may be threaded in some embodiments so that a fastener (not shown) can be threaded into the through-hole 182 and clamp the limb support 316 to the stem 58. It should be understood that in some embodiments, mount 74 may be omitted and replaced with other embodiments of mounts, such as mounts 176 or 180, for example.

Figure 17:
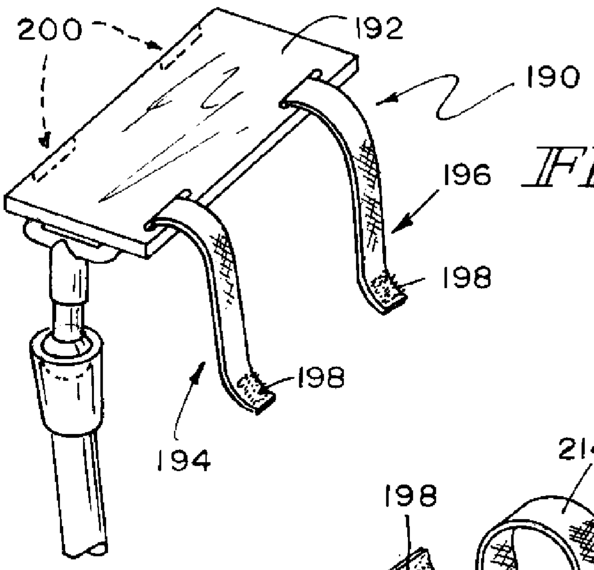
FIG. 17 is a perspective view of another embodiment of a limb support.

Referring now to FIG. 17, another embodiment of a disposable dressing 190 is supported on a limb support 16 with the disposable dressing 190 including a relatively rigid fabric covered base 192 and two straps 194 and 196 configured to overlie a patient's limb supported on the base 192. Each strap 194 and 196 includes a fastener 198 which is illustratively embodied as a hook portion of a hook-and-loop fastener system. The disposable dressing 190 further includes a pair of fasteners 200 which include loops of a hook-and-loop fastener system with the fasteners 198 engaging the fasteners 200 to secure the patient's arm to the base.

Figure 18:
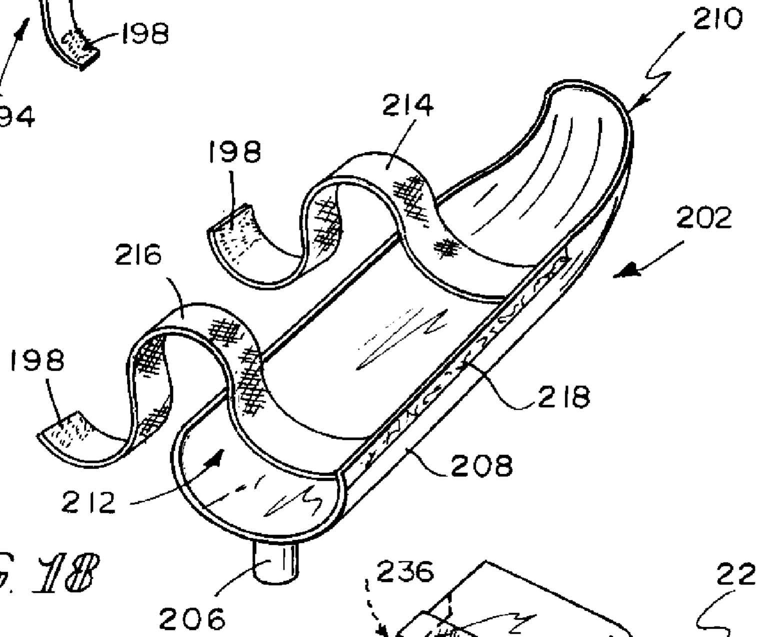
FIG. 18 is a perspective view of yet another embodiment of a limb support.

In another embodiment of a limb support 202 shown in FIG. 18, a base 204 is secured to a mount 206 and includes a rigid base 208 formed to support and restrain a forearm of a patient. The base 208 is forms a concave channel 212 in which the forearm is positioned with the fingers of the patient resting on a grip 210 so that the wrist is flexed with the hand upward. Two straps 214 and 216 each include a fastener 198 which engages a fastener strip 218 to secure the forearm. The fastener strip 218 is illustratively comprises loops of a hook-and-loop fastening system.

Figure 19:
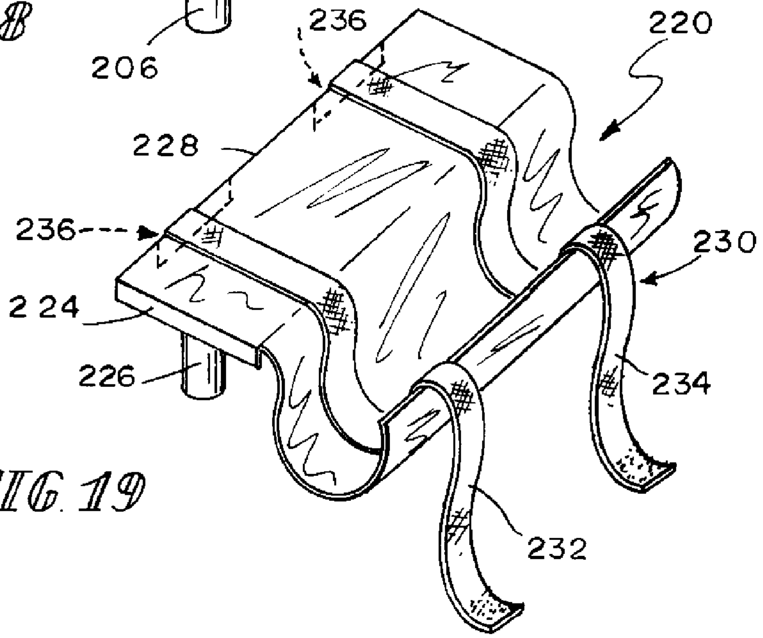
FIG. 19 is a perspective view of still yet another embodiment of a limb support.

In still another embodiment of a limb support 220 shown in FIG. 19, the limb support comprises a planar rigid base 224 coupled to a mount 226. The base 224 forms a support surface 228 on which a limb is positioned. A disposable dressing 230 is secured to the base 224 by hook-and-loop fasteners (not shown). A pair of straps 232, 234, is positioned on the surface 228 and is secured to the disposable dressing 230 by hooks (not shown) that grip the dressing 230 and are secured to loop fasteners 236, positioned on the base 224. The straps 232, 234 and disposable dressing 230 are wrapped over the limb positioned on the surface 228. The straps 232, 234 are secured to the loop fasteners 236 and wrap around the base 224 to secure to the disposable dressing 230 to secure the dressing 230 to the base 224. The straps 232, 234 and dressing 230 are disposable and the base 224 is sterilizable.

Figure 20:
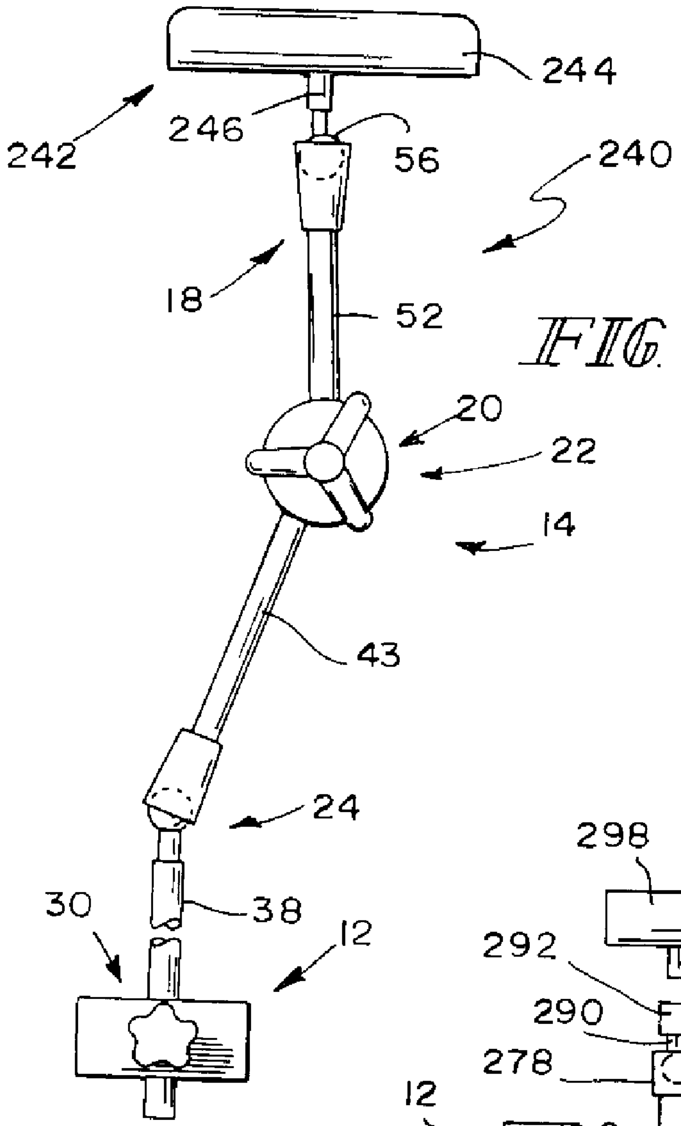
FIG. 20 is a front view of yet another embodiment of a limb positioner.
Figure 21:
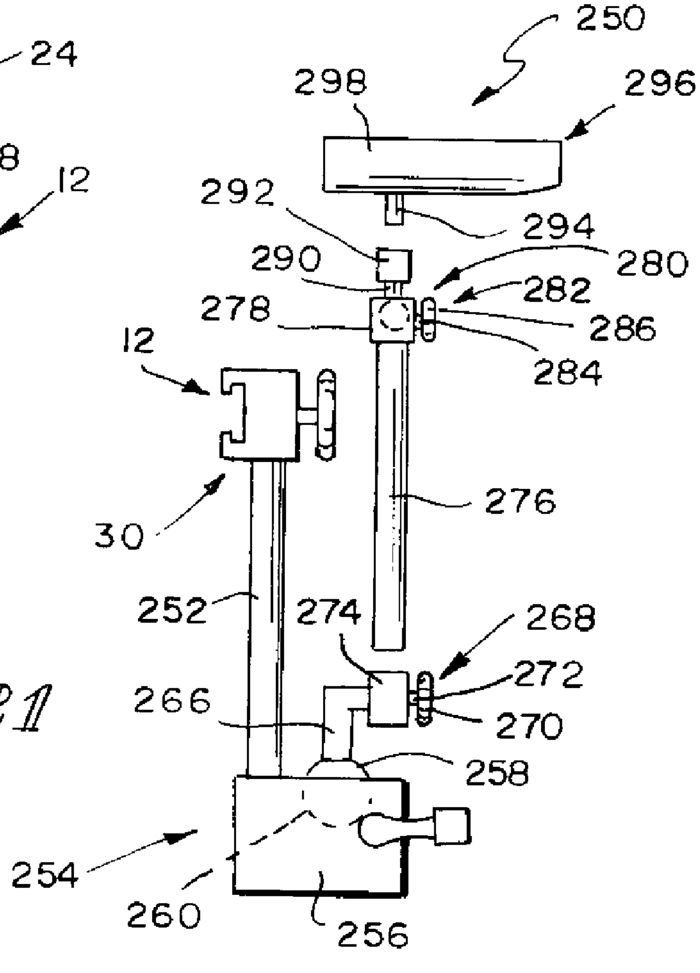
FIG. 21 is a side view of still yet another embodiment of a limb positioner.

In yet another embodiment shown in FIG. 20, a limb positioner 240 includes a multi-axis positioner 14 and a limb support 242. The limb support 242 includes a body 244 and a mount 246 supported on the stem 58 of the multi-axis positioner 14. The mount 246 is positioned mid-way along the length of the body 244 so that rotation of the limb support 242 about the center of ball 56 is indexed to the center of the body 244.

In still yet another embodiment, a limb positioner 250 includes a lock 30 secured to a rod 252 which supports a locking ball joint 254. Locking ball joint 254 comprises a body 256 supporting a ball 258 in a socket 260 formed in the body 256. The ball 258 is lockable by a cam lock 262 including a handle 264 which is movable between a first position where the ball 258 is free to move in the socket 260 and a second position where the ball 258 is locked. A stem 266 coupled to the ball 258 supports a clamp 268 including a body 274, a handle 270 and a threaded member 272. The threaded member 272 is movable in the body 274 when a user actuates the handle 270 to clamp a rod 276. The rod 276 supports a socket 278 of a ball joint 280. The ball joint 280 includes a lock 282 having a threaded member 284 and a handle 286, the threaded member 284 movable relative to the socket 278 to lock and unlock a ball 288 of the ball joint 280 when the handle 286 is actuated. A stem 290 supports a mount 292 which is configured to receive a shaft 294 of a limb support 296. The limb support 296 also includes a body 298 on which a limb is positioned to be supported by the limb positioner 250.

In some embodiments, a mount 292 could be added to the stem 58 of multi-axis positioner 14 and the mount 74 of limb support 16 could be omitted and replaced by a shaft similar to shaft 294 such that the multi-axis positioner has the male member and the limb support 16 has the female member of the connection. Similarly, the stem 38 of multi-axis positioner 14 could be positioned in clamp 268 of the limb positioner 250 so make use of the additional adjustment available for a limb positioner so configured.

The variations in embodiments disclosed herein will be understood by those of skill in the art to permit a user to configure a limb positioner in a number of ways. Within the scope of this disclosure, the configuration of the limb support may be adjusted to accommodate a number of positions of a patient's limb as illustrated in FIGS. 22-28. The embodiments of FIGS. 22-28 are meant to be illustrative of but just a few of the adaptations of the disclosed limb positioner components. The patient 136 in FIGS. 22-26 is supported on surgical table 602 with an add-on support device. Such a support device is referred to as a "beach chair." Beach chairs are available separate from a surgical table. Representative units consistent with this disclosure are available from Allen Medical System of Acton, Mass. For example part numbers A-91000 or A-90000 from Allen Medical Systems are representative commercial embodiments.

Figure 22:
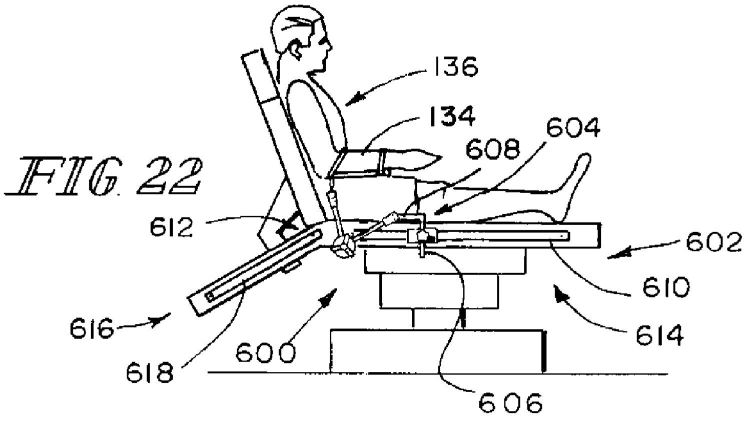
FIGS. 22-28 are side views of various embodiments of limb positioners engaged with patient support apparatuses and supporting the forearm of patient.
Figure 24:
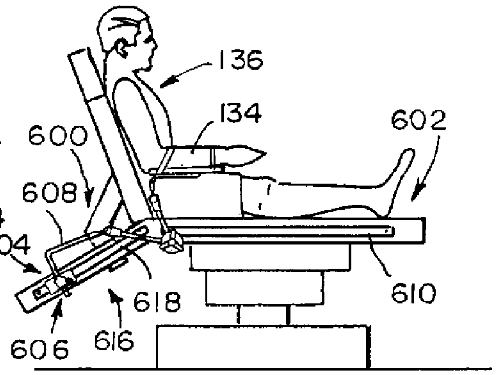

In FIG. 22, a limb positioner 600 is mounted to the rail of a surgical table 602 with the limb positioner 600 supporting the forearm 134 of a patient 136. In the illustrative embodiment of FIG. 22, the limb positioner 600 is similar to the limb positioner 10, with the stem 38 of limb positioner 10 omitted and replaced by a stem 604 which has a leg 606 and an arm 608 which extends at an approximately 90 degree angle from the leg 606 to such that the limb positioner 600 is mounted to a rail 610 of the surgical table 602 at a position spaced apart from an articulated joint 612 between a main portion 614 and head portion 616 of the surgical table 602. FIG. 24 shows the limb positioner 600 mounted to a rail 618 positioned on the head portion 616 of the surgical table 602.

Figure 23:
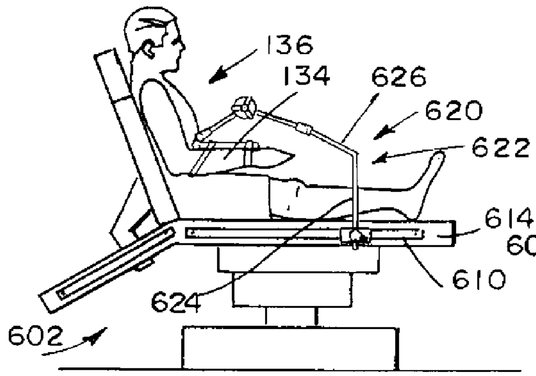

In the illustrative embodiment of FIG. 23, a limb positioner 620 is similar to limb positioner 10, with stem 38 being omitted and replaced with a stem 622 having a leg 624 and an arm 626 coupled to the leg 624 to form an angle of about 45 degrees with the leg 624. In addition, the limb support 16 of limb positioner 620 is positioned to support the forearm 134 of the patient 136 from above, permitting access to an exterior surface of the patient's elbow.

Figure 25:
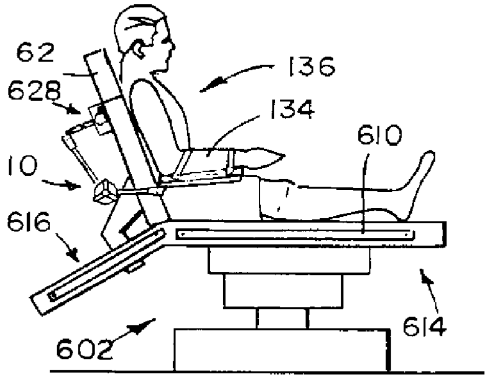
Figure 26:
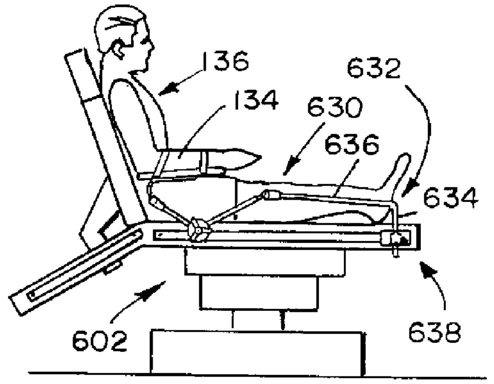

In the illustrative embodiment of FIG. 25, a limb positioner 10 is positioned directly on a frame member 626 of a beach chair 628. In the illustrative embodiment of FIG. 26, a limb positioner 630 is similar to limb positioner 600, with the 604 replaced by a stem 632 having a leg 634 and an arm 636. The arm 636 of stem 632 is longer than the leg 634 and permits the rail clamp 12 to be positioned near a foot end 638 of the rail 610.

Figure 27:
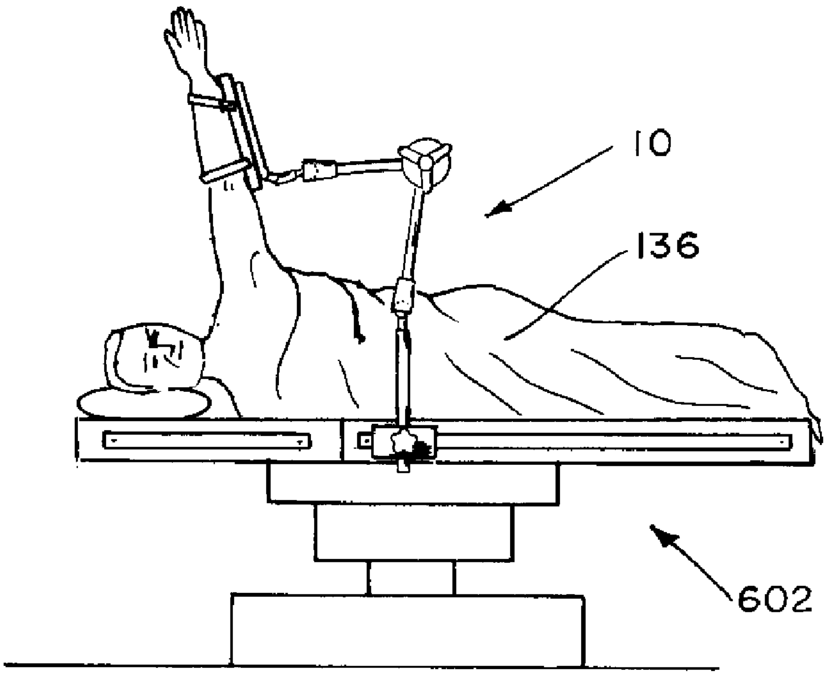

FIG. 27 is illustrative of the use of the limb positioner 10 in use when a patient 136 is in a side-lying position on the surgical table 602.

Figure 28:
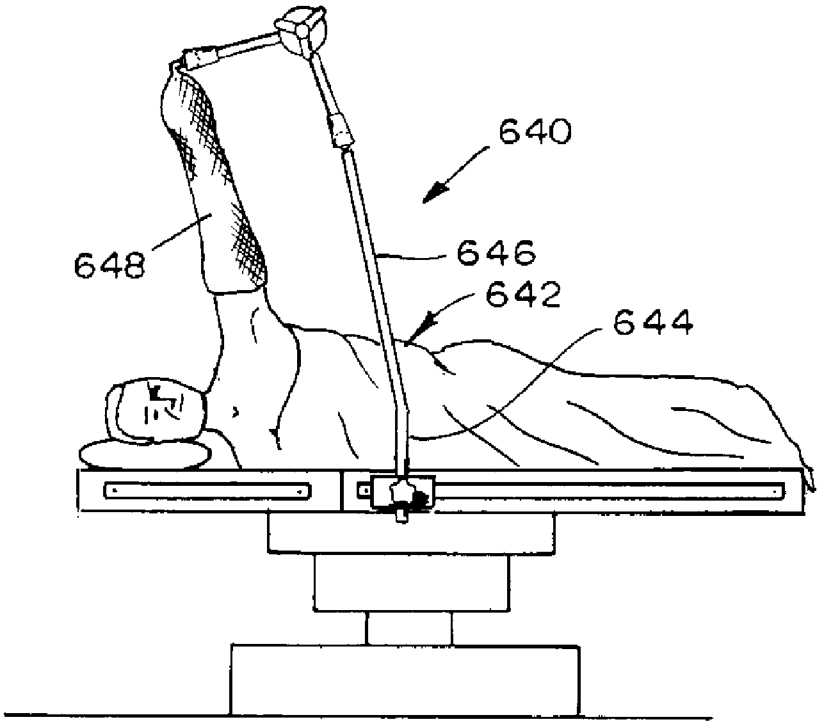

In another embodiment shown in FIG. 28, a limb positioner 640 is similar to limb positioner 610. A stem 642 of limb positioner 640 replaces the stem 38 of limb positioner 10. The stem 642 has a leg 644 and an arm 646 which extends from the leg 644 at an obtuse angle. Also, the limb support 16 is omitted and replaced with a sterile armtrap 648. A commercial embodiment of the armtrap 648 is part number A-21200 available from Allen Medical Systems.

Although certain illustrative embodiments have been described in detail above, variations and modifications exist within the scope and spirit of this disclosure as described and as defined in the following claims.

The invention claimed is:

1. A limb positioner comprising a multi-axis positioner including a variable resistance release mechanism adjustable to vary the resistance of each axis of the multi-axis positioner to movement, the multi-axis positioner including a first pivot pivotable about a first axis, a lock supporting the multi-axis positioner, the lock movable between a first position wherein the multi-axis positioner is movable relative to the lock and a second position wherein the multi-axis positioner is fixed relative to the lock, and an arm support supported by the multi-axis positioner, wherein the arm support includes a support structure configured to support an arm such that an elbow of the arm is indexed to the first pivot so that a forearm of the arm is movable with the support structure about the first axis without movement of the elbow or an upper arm.

2. The limb positioner of claim 1, wherein the multi-axis positioner comprises first and second spherical joints, first and second arms coupled to each of the respective first and second spherical joints, and a hub interposed between the first and second arms, the first arm pivotable relative to the second arm.

3. The limb positioner of claim 2, wherein the multi-axis positioner further includes a handle positioned on the hub and actuable by user, the handle operable to vary the resistance to movement of the first and second spherical joints and the hub.

4. The limb positioner of claim 3, wherein pivoting of the arm support about the first axis permits the arm to move about the joint without causing movement of the axis of the joint.

5. The limb positioner of claim 4, further comprising a disposable dressing secured to the arm support, the disposable dressing including a plurality of straps, each strap including a first fastener, each of the first fasteners engageable with a second fastener of the disposable dressing such that the straps are positioned to secure the arm of a patient to the arm support.

6. The limb positioner of claim 5, wherein the first fastener comprises a first portion of a hook-and-loop fabric fastener and the second fastener comprises a second portion of the hook-and-loop fabric fastener.

7. The limb positioner of claim 1, further comprising a disposable dressing secured to the arm support, the disposable dressing including means for securing the forearm of the patient to the arm support.

8. The limb positioner of claim 7, wherein the means for securing the forearm of the patient to the arm support includes a plurality of straps and fasteners, the straps positionable to overlie the forearm and the fasteners securing the straps to maintain the forearm positioned on the arm support.

9. The limb positioner of claim 1, wherein the variable resistance release mechanism is adjustable to a position wherein movement about each axis of the multi-axis positioner is resisted at a rate that prevents the arm supported on the limb positioner from movement under the weight of the arm while permitting a user to adjust the position of the arm by applying sufficient manual force to overcome the resistance.

10. A limb support comprising a frame including a mount having a longitudinal length defining a longitudinal axis, a cross-bar coupled to the mount, the cross-bar having a longitudinal length defining a longitudinal axis, a first extension having a longitudinal length defining a longitudinal axis, the first extension coupled to the cross-bar at a position spaced apart from the mount, the first extension extending from the cross-bar in a cantilevered configuration such that the longitudinal axis of the first extension is generally perpendicular to both the longitudinal axis of the cross-bar and the longitudinal axis of a the mount, a second extension having a longitudinal length defining a longitudinal axis, the second extension coupled to the cross-bar at a position spaced apart from the mount and opposite the first extension, the second extension extending from the cross-bar in a cantilevered configuration such that the longitudinal axis of the second extension is generally perpendicular to both the longitudinal axis of the cross-bar and the longitudinal axis of a the mount and the longitudinal axis of the second extension is generally parallel to the longitudinal axis of the first extension, a space being formed between the first extension and the second extension, and a spacer between each of the first and second extensions, the longitudinal axes of the first and second extensions are vertically spaced apart from the longitudinal axis of the cross-bar such that the longitudinal axes of the first and second extensions do not intersect the longitudinal axis of the cross-bar.

11. The limb support of claim 10, wherein the limb support further comprises a disposable dressing positioned on the first and second extensions, the disposable dressing including a plurality of flexible restraints for securing the limb of a patient to the limb support.

12. The limb support of claim 11, wherein the disposable dressing includes (i) a flexible base having a bottom surface and a top surface, (ii) an envelope having an open end, the envelope sized to enclose the first and second extensions, (iii) a fastener to securing the disposable dressing to the frame, (iv) a flap coupled to the flexible base, the flap positionable to overlie a limb supported on the flexible base, and (v) a plurality of straps to secure the flap over the limb and secure the limb to the limb support.

13. The limb support of claim 12, wherein the straps are secured by a hook-and-loop fastener.

14. The limb support of claim 12, wherein the disposable dressing comprises foam.

15. The limb support of claim 10, wherein the mount has a cavity sized to be received on a supporting structure for the mount.

16. The limb support of claim 10, wherein the limb support is sterilizable.

17. A limb positioner comprising a multi-axis positioner including a variable resistance release mechanism adjustable to vary the resistance of each axis of the multi-axis positioner to movement, the multi-axis positioner including an arm and a pivot coupled to the arm, a lock supporting the multi-axis positioner, the lock movable between a first position wherein the multi-axis positioner is movable relative to the lock and a second position wherein the multi-axis positioner is fixed relative to the lock, and a limb support supported by the pivot of the multi-axis positioner, the limb support including a mount coupled to the pivot, a first extension sized to support a lower extremity of a patient's limb, and a spacer extending between the mount and a proximal end of the first extension so that the proximal end and a distal end of the first extension are cantilevered out from the mount in a single direction.

18. The limb positioner of claim 17, wherein the variable resistance release mechanism is adjustable to a position wherein movement about each axis of the multi-axis positioner is resisted at a rate that prevents a limb supported on the limb positioner from movement under the weight of the limb while permitting a user to adjust the position of the limb by applying sufficient manual force to overcome the resistance.

19. The limb positioner of claim 17, wherein the multi-axis positioner comprises a first spherical joint, a second spherical joint, and a second arm, the first and the second arm coupled to each of the respective first and second spherical joints, and a hub interposed between the first and the second arm, the first arm pivotable relative to the second arm.

* * * * *